(12) United States Patent
Bae et al.

(10) Patent No.: US 12,274,893 B2
(45) Date of Patent: Apr. 15, 2025

(54) LED LIGHTING APPARATUS HAVING STERILIZING FUNCTION

(71) Applicant: SEOUL VIOSYS CO., LTD., Ansan-si (KR)

(72) Inventors: Hee Ho Bae, Ansan-si (KR); A Young Lee, Ansan-si (KR); Yeong Min Yoon, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 18/542,328

(22) Filed: Dec. 15, 2023

(65) Prior Publication Data

US 2024/0115876 A1 Apr. 11, 2024

Related U.S. Application Data

(63) Continuation of application No. 17/676,744, filed on Feb. 21, 2022, now Pat. No. 11,844,957, which is a
(Continued)

(51) Int. Cl.
*A61N 5/06* (2006.01)
*F21K 9/65* (2016.01)
(Continued)

(52) U.S. Cl.
CPC ............... *A61N 5/062* (2013.01); *F21K 9/65* (2016.08); *F21V 3/00* (2013.01); *H01L 25/0753* (2013.01);
(Continued)

(58) Field of Classification Search
CPC ........ A61L 2/084; A61L 2/24; A61L 2202/14; A61L 2202/11; A61L 9/20;
(Continued)

(56) References Cited

U.S. PATENT DOCUMENTS 10,309,614 B1 6/2019 Jones et al.
10,357,582 B1 7/2019 Barron et al.
(Continued)

FOREIGN PATENT DOCUMENTS

CN 108472495 8/2018
KR 10-1075411 10/2011
(Continued)

OTHER PUBLICATIONS

Examination Report dated Jan. 18, 2023, issued to Indian Patent Application No. 202117029428 (with English Translation).
(Continued)

*Primary Examiner* — Kevin Quarterman
(74) *Attorney, Agent, or Firm* — Oblon, McClelland, Maier & Neustadt, L.L.P.

(57) ABSTRACT

A lighting apparatus is disclosed. The lighting apparatus according to one embodiment of the present disclosure includes: a white light emitting device including at least one first light emitting diode and a wavelength converter to implement white light; and at least one second light emitting diode emitting light suitable for producing a cell activating substance, wherein the first light emitting diode emits light having a central wavelength in a range of about 300 nm to about 420 nm, the second light emitting diode emits light having a central wavelength in a range of about 605 nm to about 935 nm, the wavelength converter includes a plurality of wavelength conversion substances to convert light of the first light emitting diode into white light, the lighting apparatus emits the white light implemented in the white light emitting device and light generated by the second light emitting diode to the outside, and, in irradiance spectrum of the white light implemented in the white light emitting device, irradiance of the central wavelength of light emitted from the first light emitting diode is smaller than that of a
(Continued)

peak wavelength of blue light emitted from the wavelength conversion substance.

20 Claims, 7 Drawing Sheets

Related U.S. Application Data continuation of application No. 16/703,067, filed on Dec. 4, 2019, now Pat. No. 11,253,721.

(60) Provisional application No. 62/776,566, filed on Dec. 7, 2018.

(51) Int. Cl.
  *F21V 3/00* (2015.01)
  *H01L 25/075* (2006.01)
  *H01L 33/50* (2010.01)
  *H01L 33/62* (2010.01)
  *F21Y 113/13* (2016.01)
  *F21Y 115/10* (2016.01)

(52) U.S. Cl.
  CPC .......... *H01L 33/504* (2013.01); *H01L 33/505* (2013.01); *H01L 33/507* (2013.01); *H01L 33/62* (2013.01); *A61N 2005/066* (2013.01); *A61N 2005/0661* (2013.01); *A61N 2005/0663* (2013.01); *F21Y 2113/13* (2016.08); *F21Y 2115/10* (2016.08)

(58) Field of Classification Search
  CPC ... H01L 25/0753; H01L 33/62; H01L 33/507; H01L 33/505; H01L 33/504; H01L 33/502; H05B 45/10; H05B 45/20; F21Y 2115/10; F21Y 2113/13; F21K 9/62
  See application file for complete search history.

(56) References Cited

U.S. PATENT DOCUMENTS

| 10,617,774 | B2 | 4/2020 | Winslow et al. |
| 10,709,898 | B2 | 7/2020 | Mori et al. |
| 11,253,721 | B2 | 2/2022 | Bae |
| 11,844,957 | B2* | 12/2023 | Bae ................... H01L 25/0753 |
| 2012/0161170 | A1 | 6/2012 | Dubuc et al. |
| 2014/0225137 | A1 | 8/2014 | Krames et al. |
| 2016/0030610 | A1 | 2/2016 | Peterson et al. |
| 2016/0375161 | A1* | 12/2016 | Hawkins ................ H05B 47/19 422/22 |
| 2018/0035619 | A1 | 2/2018 | Ueno et al. |

FOREIGN PATENT DOCUMENTS

| KR | 10-2013-0131584 | 12/2013 |
| KR | 10-1769392 | 8/2017 |
| KR | 10-2018-0036728 | 4/2018 |
| KR | 10-1848254 | 4/2018 |

OTHER PUBLICATIONS

Extended European Search Report dated Aug. 4, 2022, for European Patent Application No. 19894012.4.
Ishiguro et al., "Effect of near-infrared light-emitting diodes on nerve regeneration". Journal of Orthopaedic Science, 2010, pp. 233-239, vol. 15, Japanese Orthopaedic Association, Japan.
Keszler et al., "Far red/near infrared light-induced protection against cardiac ischemia and reperfusion injury remains Intact under diabetic conditions and is independent of nitric oxide synthase", Frontiers in Physiology, Aug. 2014, pp. 1-7. vol. 5, United States.
International Search Report dated Mar. 20, 2020 on PCT/KR2019/017077.
Non-Final Office Action mailed Jun. 21, 2021, in U.S. Appl. No. 16/703,067.
Notice of Allowance issued Oct. 18, 2021, in U.S. Appl. No. 16/703,067.
Non-Final Office Action dated Jul. 5, 2024 issued in U.S. Appl. No. 18/541,086.

* cited by examiner

LED LIGHTING APPARATUS HAVING STERILIZING FUNCTION

CROSS-REFERENCE TO RELATED APPLICATIONS

This application is a Continuation of U.S. patent application Ser. No. 17/676,744 filed Feb. 21, 2022, which is a Continuation of Ser. No. 16/703,067, filed on Dec. 4, 2019, which claims priority to and the benefit of U.S. Provisional Application No. 62/776,566, filed on Dec. 7, 2018, each of which is hereby incorporated in its entirety by reference for all purposes as set forth herein.

TECHNICAL FIELD BACKGROUND

Exemplary embodiments of the present disclosure relate to a lighting apparatus having a cell activating function.

As an inorganic light source, light emitting diodes have been used in various fields including displays, vehicular lamps, general lighting, and the like. In particular, with various advantages such as long lifespan, low power consumption, and rapid response, light emitting diodes have been replacing existing light sources in the art.

Meanwhile, sunlight exhibits a broad spectrum of wavelengths in the ultraviolet, visible and infrared regions. The human body has survived by adapting to sunlight, and in particular, cells in the human body absorb light of wavelengths near the near infrared to use for cell activity.

Meanwhile, it is well known that ultraviolet rays are generally harmful to the human body, particularly the eyes or skin. In addition, some wavelength bands in the blue wavelength region may cause eye diseases or skin diseases.

SUMMARY

Exemplary embodiments of the present disclosure provide a lighting apparatus having a cell activating function without causing eye diseases, skin diseases and the like, and a lighting system having the same.

Exemplary embodiments of the present disclosure provide a lighting apparatus capable of changing color temperature over time like sunlight and having a cell activating function and a lighting system having the same.

Exemplary embodiments of the present disclosure provide a lighting apparatus capable of changing color temperature in consideration of the color temperature of sunlight according to a region and time and having a cell activating function, and a lighting system having the same.

An exemplary embodiment of the present disclosure provides a light emitting apparatus, including: a white light emitting device including at least one first light emitting diode and a wavelength converter to implement white light; and at least one second light emitting diode emitting light suitable for producing a cell activating substance, wherein the first light emitting diode emits light having a central wavelength in a range of about 300 nm to about 420 nm, the second light emitting diode emits light having a central wavelength in a range of about 605 nm to about 935 nm, the wavelength converter includes a plurality of wavelength conversion substances to convert light of the first light emitting diode into white light, the lighting apparatus emits the white light implemented in the white light emitting device and light generated by the second light emitting diode to the outside, and, in irradiance spectrum of the white light implemented in the white light emitting device, irradiance of the central wavelength of light emitted from the first light emitting diode is smaller than that of a peak wavelength of blue light emitted from the wavelength conversion substance.

An exemplary embodiment of the present disclosure provides a light emitting apparatus, including: a first light emitting unit including a first first-light emitting diode emitting light having a central wavelength in a range of about 300 nm to about 420 nm and a first wavelength converter; a second light emitting unit including a first second-light emitting diode emitting light having a central wavelength in a range of about 300 nm to about 470 nm and a second wavelength converter; at least one second light emitting diode emitting light having a central wavelength in a range of about 605 nm to about 935 nm, wherein the first light emitting unit emits light of a higher color temperature than that of the second light emitting unit, the first wavelength converter includes a blue wavelength conversion substance for converting light emitted from the first first-light emitting diode into blue light, and, in irradiance spectrum of light emitted to the outside, irradiance of the central wavelength of light generated by each light emitting diode in the first and second light emitting units and emitted to the outside without wavelength conversion is smaller than that of a peak wavelength of wavelength-converted light emitted from the first and second wavelength converters.

In addition, embodiments of the present disclosure provide a lighting system including the lighting apparatus mentioned above.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION

Figure 1:
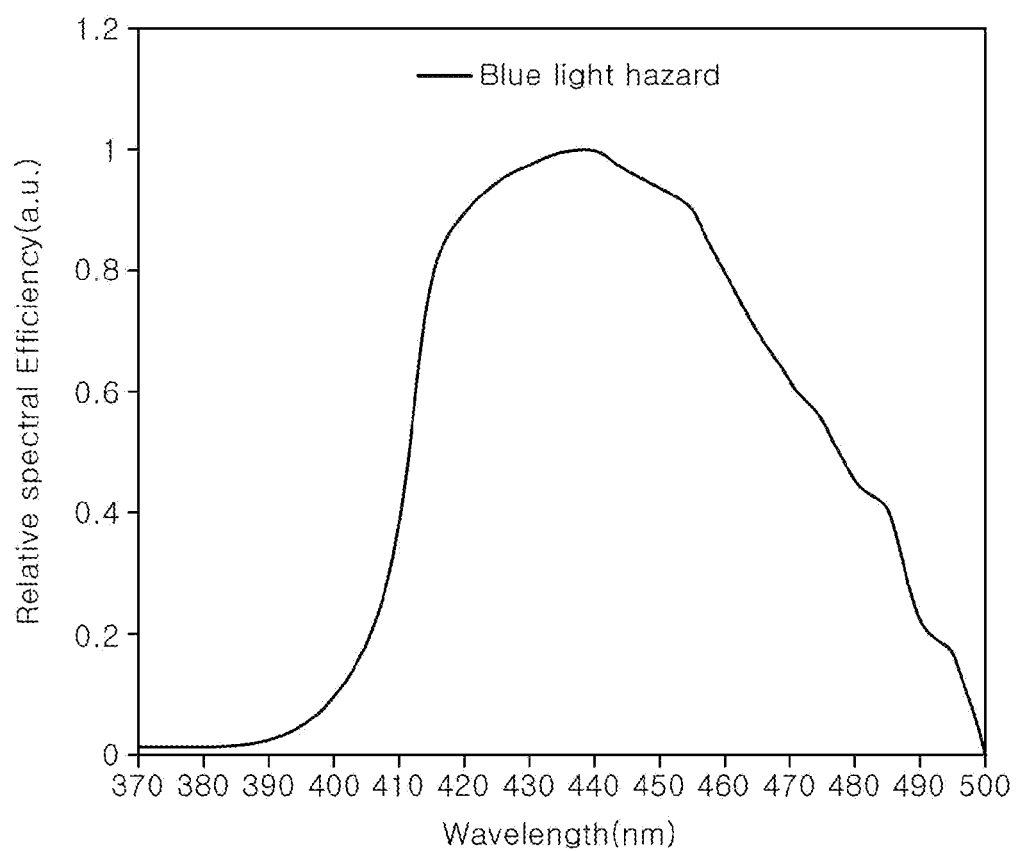
FIG. 1 is a graph showing a degree of hazard according to wavelengths of blue light.

Hereinafter, exemplary embodiments of the present disclosure will be described in detail with reference to the accompanying drawings. The following embodiments are provided by way of example so as to fully convey the spirit of the present disclosure to those skilled in the art to which the present disclosure pertains. Accordingly, the present disclosure is not limited to the embodiments disclosed herein and can also be implemented in different forms. In the drawings, widths, lengths, thicknesses, and the like of elements can be exaggerated for clarity and descriptive purposes. When an element or layer is referred to as being "disposed above" or "disposed on" another element or layer, it can be directly "disposed above" or "disposed on" the other element or layer or intervening elements or layers can be present. Throughout the specification, like reference numerals denote like elements having the same or similar functions.

A lighting apparatus according to one embodiment of the present disclosure includes: a white light emitting device including at least one first light emitting diode and a wavelength converter to implement white light; and at least one second light emitting diode emitting light suitable for producing a cell activating substance, wherein the first light emitting diode emits light having a central wavelength in a range of about 300 nm to about 420 nm, the second light emitting diode emits light having a central wavelength in a range of about 605 nm to about 935 nm, the wavelength converter includes a plurality of wavelength conversion substances to convert light of the first light emitting diode into white light, the lighting apparatus emits the white light implemented in the white light emitting device and light generated by the second light emitting diode to the outside, and, in irradiance spectrum of the white light implemented in the white light emitting device, irradiance of the central wavelength of light emitted from the first light emitting diode is smaller than that of a peak wavelength of blue light emitted from the wavelength conversion substance.

The lighting apparatus having a cell activating function may be provided by using the second light emitting diode suitable for producing a cell activating substance together with the white light emitting device. Since irradiance of light emitted from the first light emitting diode is smaller than that of the peak wavelength of blue light emitted from the wavelength conversion substance, the lighting apparatus may prevent the first light emitting diode from causing harm to the human body or from causing eye diseases or skin diseases.

The cell activating substance may be nitric oxide (NO) produced by cytochrome c oxidase activity in mitochondria. NO improves the health of the human body by affecting pain relief and improving blood circulation.

Further, light of the second light emitting diode absorbed by the intracellular mitochondria causes the mitochondria to produce more ATPs and enhance metabolism.

The second light emitting diode may emit light having a central wavelength of about 605 nm to about 655 nm, about 685 nm to about 705 nm, about 790 nm to about 840 nm, or about 875 nm to about 935 nm. In these wavelength ranges, an energy absorption rate of cytochrome c oxidase is relatively higher. In particular, the cytochrome c oxidase exhibits the highest absorption in the range of 790 nm to 840 nm, and followed by in the range of 875 nm to 935 nm. Accordingly, the second light emitting diode may include a light emitting diode having a central wavelength at least in the range of 790 nm to 840 nm or in the range of 875 nm to 935 nm.

In one embodiment, the wavelength converter may include wavelength conversion substances for converting light of the first light emitting diode into blue, green and red light. In another embodiment, the wavelength converter may include blue and orange wavelength conversion substances for converting light of the first light emitting diode into blue and orange light.

The white light and light emitted from the second light emitting diode may be mixed and emitted. For example, the lighting apparatus may further include a diffusion plate for mixing the white light and light emitted from the second light emitting diode.

Meanwhile, the wavelength converter may include a phosphor or a quantum dot. For example, the wavelength converter may include a blue phosphor, a green phosphor and a red phosphor. In embodiments, these phosphors may be replaced individually or all with quantum dots.

In one embodiment, light emitted from the second light emitting diode may be emitted to the outside without passing through the wavelength converter. In another embodiment, a portion of light emitted from the second light emitting diode may be wavelength-converted by the wavelength converter.

Meanwhile, the first light emitting diode may emit light having a central wavelength in a range of about 400 nm to about 420 nm. Compared with a case of using ultraviolet rays, light having the wavelength within this range may be used, thereby improving a light conversion efficiency.

Meanwhile, irradiance of light generated by the at least one second light emitting diode and emitted to the outside may be greater than that of red light wavelength-converted by the wavelength converter and emitted. Accordingly, the cell activating substance may be produced using the second light emitting diode.

The lighting apparatus may include a greater number of first light emitting diodes than that of the at least one second light emitting diode. Accordingly, the irradiance of the white light emitting device is greater than that of the second light emitting diode.

Meanwhile, irradiance of light generated by the at least one second light emitting diode and emitted to the outside may be smaller than or equal to 570 $W/m^2$.

The lighting apparatus may further include a circuit board for mounting the first light emitting diode and the second light emitting diode.

Meanwhile, the lighting apparatus may include a location information receiver for receiving location information; and a controller for receiving the location information from the location information receiver and controlling a dose of light emitted from the white light emitting device; wherein the controller may calculate a dose of light to be emitted by the white light emitting device based on the location information, and may control the white light emitting device to emit light in an amount equivalent to the dose.

In an embodiment, the controller may calculate an appropriate dose based on the location information provided by the location information receiver, and may control the light source to emit the appropriate dose.

In another embodiment, the location information receiver may calculate location information of the lighting apparatus, the controller may receive the location information and calculate a dose of external light and an appropriate dose at the place where the lighting apparatus is located, and may control the white light emitting device to emit light in an amount equivalent to a difference between the appropriate dose and the dose of external light.

In an embodiment, the controller may calculate time information from the location information and may control a dose of light to be emitted by the white light emitting device according to the time information.

A lighting apparatus according to another embodiment of the present disclosure includes: a first light emitting unit including a first first-light emitting diode emitting light having a central wavelength in a range of about 300 nm to about 420 nm and a first wavelength converter; a second light emitting unit including a first second-light emitting diode emitting light having a central wavelength in a range of about 300 nm to about 470 nm and a second wavelength converter; at least one second light emitting diode emitting light having a central wavelength in a range of about 605 nm to about 935 nm, wherein the first light emitting unit emits light of a higher color temperature than that of the second light emitting unit, the first wavelength converter includes a blue wavelength conversion substance for converting light emitted from the first first-light emitting diode into blue light, and, in irradiance spectrum of light emitted to the outside, irradiance of the central wavelength of light generated by each light emitting diode in the first and second light emitting units and emitted to the outside without wavelength conversion is smaller than that of a peak wavelength of wavelength-converted light emitted from the first and second wavelength converters.

Since a plurality of light emitting units are included, a lighting apparatus capable of implementing white light having various color temperatures may be provided. Accordingly, the lighting apparatus may change the color temperature to suit the change of sunlight over time. In addition, intensity of blue light emitted from the light emitting diodes of the lighting apparatus to the outside is made to be less than that of light wavelength-converted by the wavelength converter, and thus the occurrence of eye diseases and skin diseases caused by the light emitting diode may be prevented.

Moreover, the lighting apparatus may further include a third light emitting unit including a first third-light emitting diode emitting light having a central wavelength in a range of about 300 nm to about 470 nm and a third wavelength converter, wherein the third light emitting unit emits light of a higher color temperature than that of the second light emitting unit, and, in irradiance spectrum of light emitted to the outside, irradiance of the central wavelength of light generated by the first third-light emitting diode in the third light emitting unit and emitted to the outside without wavelength conversion is smaller than that of a peak wavelength of wavelength-converted light emitted from the third wavelength converter.

Meanwhile, the first to third wavelength converters may further include a green wavelength conversion substance for converting light emitted from the first light emitting diode into green light and a red wavelength conversion substance for converting light emitted from the first light emitting diode into red light, respectively. Accordingly, the first to third light emitting units may implement white light, respectively.

The first light emitting unit, the second light emitting unit and the third light emitting unit may be driven independently of one another.

The first first- to first third-light emitting diodes may emit light having a central wavelength in a range of about 400 nm to about 420 nm. The first first- to first third-light emitting diodes may emit light having the same peak wavelength, but are not limited thereto.

Meanwhile, the cell activating substance may be nitric oxide (NO) produced by cytochrome c oxidase activity in mitochondria. Further, light of the second light emitting diode absorbed by the intracellular mitochondria causes the mitochondria to produce more ATPs and enhance metabolism.

Furthermore, the second light emitting diode may emit light having a central wavelength of about 605 nm to about 655 nm, about 685 nm to about 705 nm, about 790 nm to about 840 nm, or about 875 nm to about 935 nm. In these wavelength ranges, an energy absorption rate of the cytochrome c oxidase is relatively higher.

Light wavelength-converted by the wavelength converter and light emitted from the second light emitting diode may be mixed and emitted to the outside. The mixed light may be white light.

Furthermore, the lighting apparatus may further include a diffusion plate suitable for mixing light wavelength-converted by the wavelength converter and light emitted from the second light emitting diode.

Meanwhile, the first first- to first third-light emitting diodes may be disposed more than the at least one second light emitting diode, respectively.

The lighting apparatus may further include a circuit board on which the first first- to first third-light emitting diodes and the second light emitting diode are mounted.

In an embodiment, the lighting apparatus may further include a location information receiver for receiving location information, and a controller for controlling a dose of light emitted from the first to third light emitting units, wherein the controller may control the dose of light emitted from the first to third light emitting units based on the location information. In an embodiment, the controller may calculate an appropriate dose based on the location information provided by the location information receiver, and may control the first to third light emitting units to emit the appropriate dose.

In an embodiment, the location information receiver may calculate location information of the lighting apparatus, the controller may receive the location information and calculate a dose of external light and an appropriate dose at the place where the lighting apparatus is located, and may control the first to third light emitting units to emit light in an amount equivalent to a difference between the appropriate dose and the dose of external light.

In an embodiment, the controller may calculate time information from the location information and may control a dose of the light according to the time information.

A lighting system according to other embodiments of the present disclosure includes a lighting apparatus installed indoors, wherein the lighting apparatus is one of the lighting apparatuses described above.

Hereinafter, embodiments of the present disclosure will be described in detail with reference to the accompanying drawings.

FIG. 1 is a graph showing a degree of hazard according to wavelengths of blue light.

Blue light is known to cause eye diseases and skin diseases. In particular, blue light exhibits the highest degree of hazard between 430 nm and 440 nm. A wavelength range of 420 nm to 455 nm exhibits 90% or more degree of hazard based on the highest hazard value, that of 413 nm to 465 nm exhibits 70% or more degree of hazard, and that of 411 nm to 476 nm exhibits 50% or more degree of hazard.

Meanwhile, ultraviolet rays harm the human body and exhibit the highest degree of hazard, especially between 270 nm and 280 nm.

Figure 2:
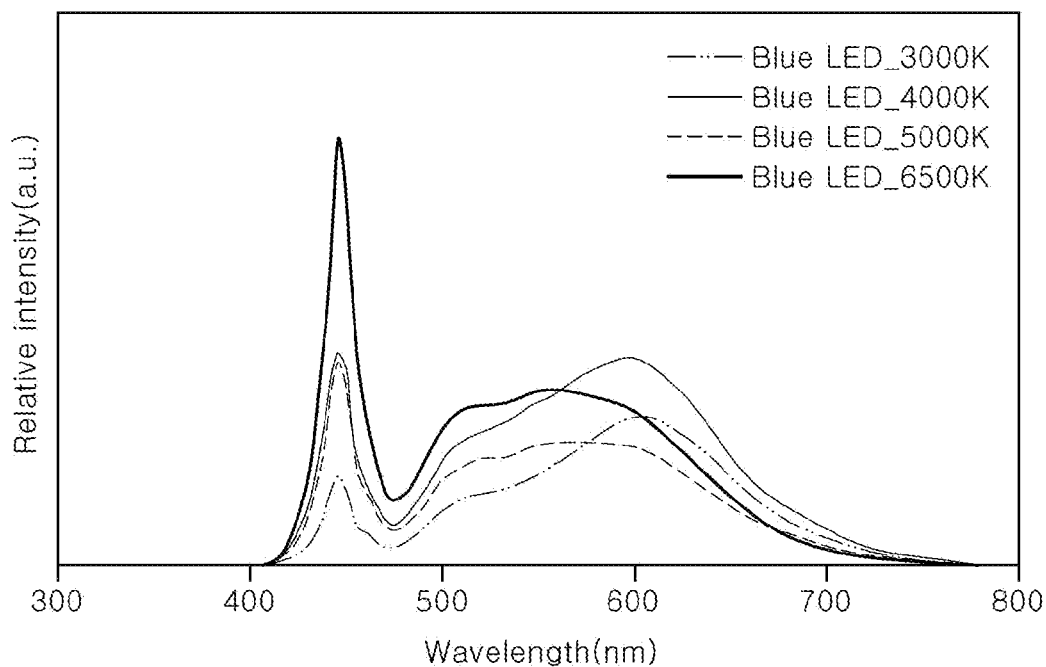
FIG. 2 shows a spectrum of a white light source using a blue light emitting diode according to a prior art.

FIG. 2 shows a spectrum of a white light source using a blue light emitting diode according to the conventional art.

Referring to FIG. 2, the white light source according to the conventional art implements white light using a yellow phosphor, or a green phosphor and a red phosphor together with a blue light emitting diode. A type of phosphor and an amount of phosphor are controlled according to a color temperature, and an intensity of the blue light increases as the color temperature increases.

A blue light emitting diode used in the conventional white light source generally has a central wavelength (peak wavelength) in a range of 430 nm to 470 nm. Blue light in this range has a relatively high degree of hazard as shown in FIG. 1. Therefore, as the color temperature of the white light source increases, the intensity of the blue light increases, thereby increasing the hazard of causing eye diseases or skin diseases.

Figure 3:
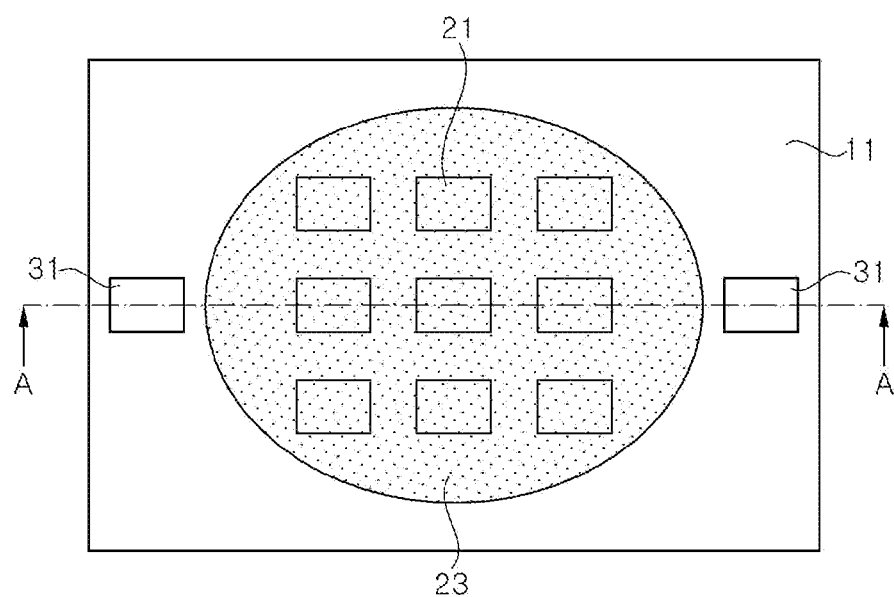
FIG. 3 is a schematic plan view illustrating a lighting apparatus according to one embodiment of the present disclosure.
Figure 4:
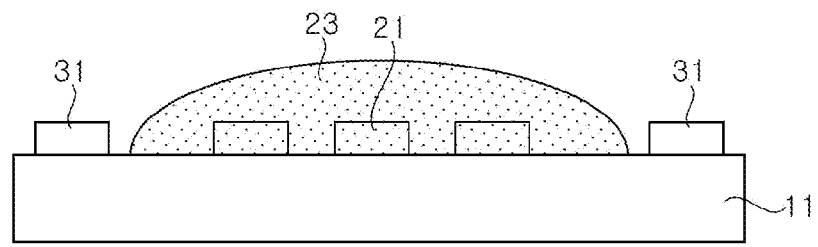
FIG. 4 is a schematic cross-sectional view taken along the line A-A of FIG. 3.

FIG. 3 is a schematic plan view illustrating a lighting apparatus according to one embodiment of the present disclosure, and FIG. 4 is a schematic cross-sectional view taken along the line A-A of FIG. 3.

Referring to FIG. 3 and FIG. 4, the lighting apparatus may include a circuit board 11, a first light emitting diode 21, a wavelength converter 23 and a second light emitting diode 31.

The circuit board 11 may have a circuit pattern for supplying power to the first and second light emitting diodes 21 and 31. The circuit board 11 may be a printed circuit board, for example, a metal-PCB.

At least one first light emitting diode 21 is mounted on the circuit board 11 as a light source for implementing the white light. A plurality of first light emitting diodes 21 may be electrically connected to one another in various ways, for example, may be connected in series, in parallel or in series parallel.

The first light emitting diode 21 may have, for example, a central wavelength in a range of about 300 nm to 420 nm, and may further have a central wavelength in a range of 400 nm to 420 nm. In addition, since the first light emitting diode 21 has the central wavelength in this range, a substantial portion of light emitted from the first light emitting diode 21 may be wavelength-converted by the wavelength converter 23. When the first light emitting diode 21 emits ultraviolet rays, most of ultraviolet rays are wavelength-converted by the wavelength converter 23, thereby preventing ultraviolet rays from being emitted to the outside. Furthermore, when the first light emitting diode having the central wavelength in the range of 400 nm to 420 nm is used, safety problems caused by ultraviolet rays may be eliminated in advance.

The wavelength converter 23 converts a wavelength of light emitted from the first light emitting diode 21. The wavelength converter 23 may be, for example, a molding member containing a phosphor or a quantum dot. The wavelength converter 23 covers the first light emitting diode 21. When the plurality of first light emitting diodes 21 are mounted on the circuit board 11, the wavelength converter 23 may cover all of the plurality of first light emitting diodes 21.

The wavelength converter 23 includes a wavelength conversion substance for implementing the white light together with light of the first light emitting diode 21. In one embodiment, the wavelength converter 23 may include a blue phosphor, a green phosphor and a red phosphor. In another embodiment, the wavelength converter 23 may include a blue phosphor and an orange phosphor. In another embodiment, the wavelength converter may include a quantum dot.

Examples of the blue phosphor may include a BAM-based, a Halo-Phosphate-based or an aluminate-based phosphor, and may include, for example, $BaMgAl_{10}O_{17}:Mn^{2+}$, $BaMgAl_{12}O_{19}:Mn^{2+}$ or $(Sr,Ca,Ba)PO_4Cl:Eu^{2+}$. The blue phosphor may have, for example, a peak wavelength in a range of 440 nm to 500 nm.

Examples of the green phosphor may include $LuAG(Lu_3(Al,Gd)_5O_{12}:Ce^{3+})$, $YAG(Y_3(Al,Gd)_5O_{12}:Ce^{3+})$, $Ga$—$LuAG((Lu,Ga)_3(Al,Gd)_5O_{12}:Ce^{3+})$, $Ga$-$YAG$ $((Ga,Y)_3(Al,Gd)_5O_{12}:Ce^{3+})$, $LuYAG((Lu,Y)_3(Al,Gd)_5O_{12}:Ce^{3+})$, Ortho-Silicate $((Sr,Ba,Ca,Mg)_2SiO_4:Eu^{2+})$, Oxynitride $((Ba,Sr,Ca)Si_2O_2N_2:Eu^{2+})$, or Thio Gallate $(SrGa_2S_4:Eu^{2+})$. The green phosphor may have a peak wavelength in a range of 500 nm to 600 nm.

Examples of the red phosphor may include a Nitride-based, a Sulfide-based, a Fluoride or an Oxynitride-based phosphor, and, specifically, may include $CASN(CaAlSiN_3:Eu^{2+})$, $(Ba,Sr,Ca)_2Si_5N_8:Eu^{2+}$, $(Ca,Sr)S_2:Eu^{2+})$, or $(Sr,Ca)_2SiS_4:Eu^{2+}$. The red phosphor may have a peak wavelength in a range of 600 nm to 700 nm.

Figure 5:
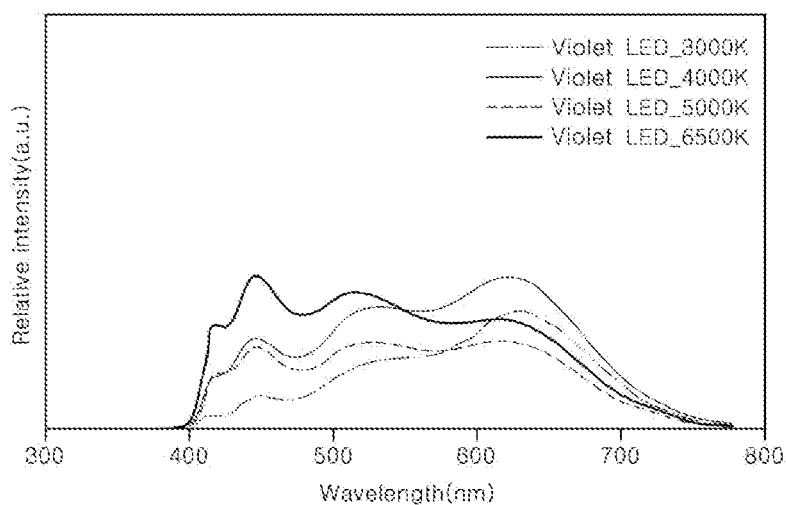
FIG. 5 shows representative spectra of a lighting apparatus according to one embodiment of the present disclosure.

White light may be implemented by a combination of the first light emitting diode 21 and the wavelength converter 23. FIG. 5 shows spectra of white light having various color temperatures implemented by the combination of the first light emitting diode 21 and the wavelength converter 23.

As shown in FIG. 5, white light of each color temperature is implemented by the combination of light emitted from the first light emitting diode and light emitted from the phosphors. In addition, it can be confirmed that irradiance of light emitted from the first light emitting diode 21 at all color temperatures is smaller than that of light emitted from the blue phosphor. As the color temperature increases, although the irradiance of light emitted from the first light emitting diode 21 also increases, the irradiance of blue light emitted from the blue phosphor increases even more. In addition, the irradiance of light emitted from the first light emitting diode may be smaller than that of light emitted from the green phosphor and may be smaller than that of light emitted from the red phosphor.

Accordingly, the lighting apparatus may prevent eye diseases or skin diseases from being caused by light emitted from the first light emitting diode.

Referring back to FIG. 3 and FIG. 4, the second light emitting diode 31 may be spaced apart from the wavelength converter 23 to be mounted on the circuit board 11. Light emitted from the second light emitting diode 31 may be emitted to the outside without actually entering the wavelength converter 23. Accordingly, irradiance of light emitted from the second light emitting diode 31 may be improved.

The second light emitting diode 31 may be connected to the first light emitting diode 21 in series or in parallel, or may be driven independently from the first light emitting diode 21.

Meanwhile, the second light emitting diode 31 emits light suitable for cell activation. The second light emitting diode 31 may emit light having a central wavelength in a range of, for example, about 605 nm to about 935 nm.

Red light or near infrared light in the range of about 605 nm to about 935 nm produces a cell activating substance in the mitochondria. Specifically, the cytochrome c oxidase in the mitochondria absorbs light in the range of about 605 nm to about 935 nm as a photoreceptor to increase its activity, thereby producing NO. NO improves human health by affecting pain relief and improving blood circulation. In addition, the activity of the cytochrome c oxidase protein contributes to ATP production, and also affects cell damage treatment.

In particular, the second light emitting diode may emit light having a central wavelength in a range of about 605 nm to about 655 nm, about 685 nm to about 705 nm, about 790 nm to about 840 nm, or about 875 nm to about 935 nm. In these wavelength ranges, an energy absorption rate of cytochrome c oxidase is relatively higher. In particular, the cytochrome c oxidase exhibits the highest absorption in the range of 790 nm to 840 nm, followed by in the range of 875 nm to 935 nm, and then in the range of 605 nm to 655 nm.

The second light emitting diode 31 emitting light having the wavelength of the relatively high energy absorption of the cytochrome c oxidase is included, and thus efficiency of health promotion may be improved.

Furthermore, when a plurality of second light emitting diodes 31 are used, it is possible to use the plurality of light emitting diodes emitting light in a specific wavelength range among the above wavelength ranges, for example, in the high efficiency range of 790 nm to 840 nm or 875 nm to 935 nm, and various light emitting diodes may be used to evenly emit light in each of the wavelength ranges.

In addition, since the light emitting diode emitting light in the range of 605 nm to 655 nm may affect the color temperature of the white light, light emitting diodes emitting light having a central wavelength in a low visibility range, that is, in the range of about 685 nm to about 705 nm, about 790 nm to about 840 nm, or about 875 nm to about 935 nm may be mainly used, not to affect the color temperature of the white light emitting device.

In the present embodiment, to add the cell activating function to the lighting apparatus, the irradiance of light emitted from the second light emitting diode 31 is greater than that at the same wavelength of light emitted from the white light emitting device. Furthermore, the irradiance of light emitted from the second light emitting diode 31 may be greater than that of light emitted to the outside of the lighting apparatus from the first light emitting diode 21 having the central wavelength in the range of 300 nm to 420 nm. Accordingly, the lighting apparatus of the present embodiment has the major cell activating function provided by the second light emitting diode 31, compared to the first light emitting diode 21.

Meanwhile, although a driving time of the second light emitting diode 31 and that of the first light emitting diode 21 may be the same, the present disclosure is not limited thereto, and the driving time of the second light emitting diode 31 may be adjusted according to an installation location of the lighting apparatus. In particular, a period of use of the second light emitting diode 31 or a magnitude of the irradiance may be adjusted in consideration of the hazard to the human body.

For example, the irradiance of the second light emitting diode 31 emitted from the lighting apparatus may be 570 W/m2 or less, and further, may be 100 W/m2 or less. 570 W/m2 represents a limit value of risk group 1 for light in the infrared range in the Photobiological Safety Standard (IEC 62471), and 100 W/m2 corresponds to an exempt. The lighting apparatus has the radiance of 570 W/m2 or less, and thus the lighting apparatus may be driven to produce a cell activating substance without harming the human body for a relatively long period of time.

In one embodiment, the lighting apparatus may include more the first light emitting diodes than the second light emitting diode, and thus may emit light of intensity suitable for illumination. However, the present disclosure is not limited thereto.

According to the present embodiment, the lighting apparatus may be used to promote the health of the human body not only in the indoor living space but also in a space where a large number of people are active such as an airport or a hospital.

Figure 6:
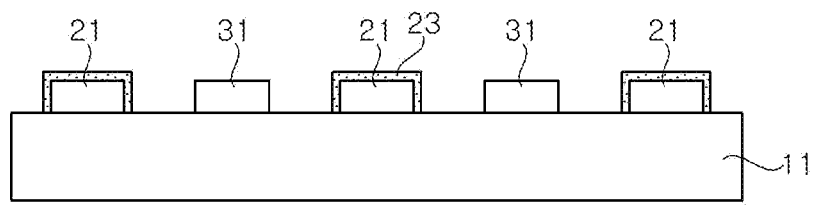
FIG. 6 is a schematic cross-sectional view illustrating a lighting apparatus according to another embodiment of the present disclosure.

FIG. 6 is a schematic cross-sectional view illustrating a lighting apparatus according to another embodiment of the present disclosure.

Referring to FIG. 6, the lighting apparatus according to the present embodiment is generally similar to the lighting apparatus described with reference to FIG. 3 and FIG. 4 except that wavelength converters 23 are formed on the first light emitting diodes 21, respectively. That is, the wavelength converter 23 in FIG. 3 and FIG. 4 covers all of the plurality of first light emitting diodes 21, but in this embodiment, each of the first light emitting diodes 21 is individually covered with the wavelength converter 23.

The wavelength conversion substances in the first light emitting diode 21 and the wavelength converter 23 are the same as those described above, and thus a detailed description thereof will be omitted.

Meanwhile, since the first light emitting diodes 21 are respectively covered with the wavelength converters 23, the second light emitting diode 31 may be disposed between the first light emitting diodes 21. That is, as shown in the drawing, the second light emitting diodes 31 may be uniformly disposed between the first light emitting diodes 21, and thus light emitted from the second light emitting diode 31 may be mixed with the white light. As a result, the lighting apparatus of the present disclosure is capable of mitigating the external recognition of light emitted from the second light emitting diode 31. The second light emitting diodes 31 may be covered with a transparent molding member to protect it from the external environment.

In the present embodiment, the second light emitting diodes 31 may be connected in series or in parallel to the first light emitting diodes 21, but the present disclosure is not limited thereto, and the second light emitting diodes 31 may be mounted on the circuit board 11 to be driven independently from the first light emitting diodes 21.

Figure 7:
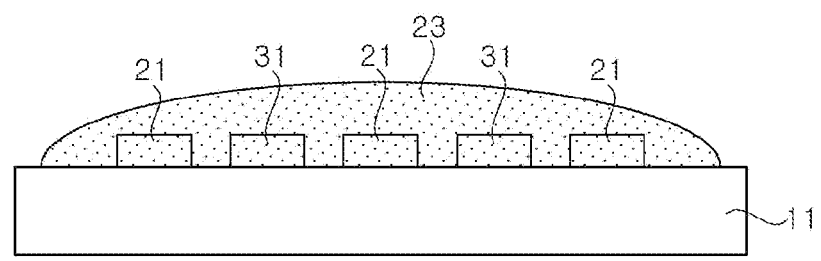
FIG. 7 is a schematic cross-sectional view illustrating a lighting apparatus according to another embodiment of the present disclosure.

FIG. 7 is a schematic cross-sectional view illustrating a lighting apparatus according to another embodiment of the present disclosure.

Referring to FIG. 7, the lighting apparatus according to the present embodiment is generally similar to the lighting apparatus described with reference to FIG. 3 and FIG. 4 except that the second light emitting diode 31 is also covered with the wavelength converter 23.

That is, the wavelength converter 23 covers not only the first light emitting diode 21 but also the second light emitting diode 31. Since the second light emitting diode 31 generally emits light having a longer wavelength than that of light emitted from the wavelength conversion substance in the wavelength converter 23, for example, a phosphor, light emitted from the second light emitting diode 31 may be emitted to the outside without being wavelength-converted by the wavelength converter 23.

However, a portion of the light emitted from the second light emitting diode 31 may be absorbed by the wavelength converter 23 and lost, and thus, more second light emitting diodes 31 than those in the previous embodiments may be used to implement the irradiance suitable for cell activation. Meanwhile, light generated by the second light emitting diode 31 may also be used to implement white light.

Meanwhile, the second light emitting diodes 31 may be uniformly disposed between the first light emitting diodes 21, and thus uniform light may be emitted to the outside. However, the present disclosure is not necessarily limited thereto.

Meanwhile, when the first light emitting diode 21 emits light having the central wavelength in the range of 300 nm to 420 nm, the number and intensity of the second light emitting diodes 31 are adjusted so that the irradiance of light generated by the second light emitting diodes 31 and emitted to the outside without wavelength conversion is greater than that of light generated in the first light emitting diodes 21 and emitted to the outside without wavelength conversion.

Accordingly, the lighting apparatus according to the present embodiment also provides an effective cell activating function by the second light emitting diode 31.

Figure 8:
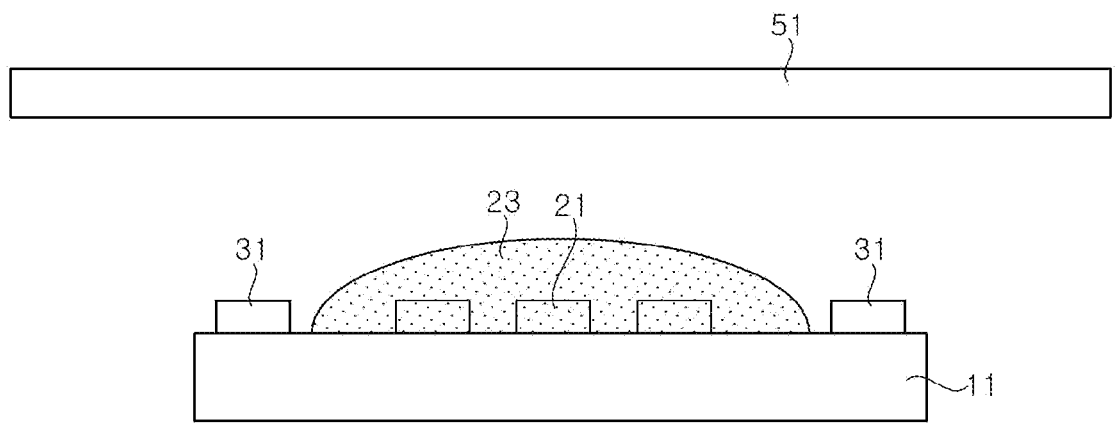
FIG. 8 is a schematic cross-sectional view illustrating a lighting apparatus according to another embodiment of the present disclosure.

FIG. 8 is a schematic cross-sectional view illustrating a lighting apparatus according to another embodiment of the present disclosure.

Referring to FIG. 8, the lighting apparatus according to the present embodiment is generally similar to the lighting apparatus described with reference to FIG. 3 and FIG. 4 except that it further includes a diffusion plate 51.

The diffusion plate 51 uniforms light by mixing the white light and light emitted from the second light emitting diode 31. Accordingly, visibility of light emitted from the second light emitting diode 31 may be reduced.

Figure 9:
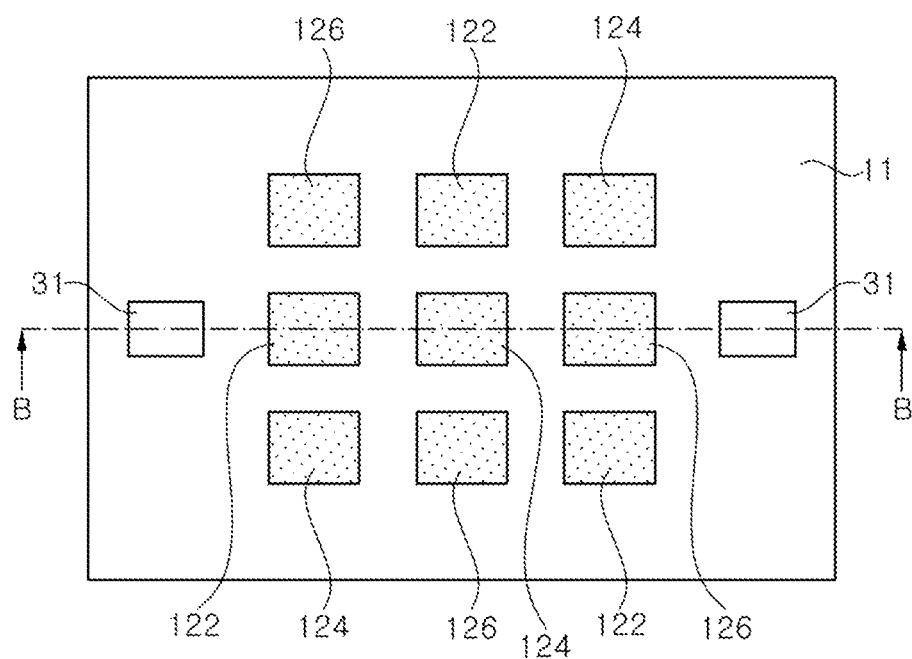
FIG. 9 is a schematic cross-sectional view illustrating a lighting apparatus according to another embodiment of the present disclosure.
Figure 10:
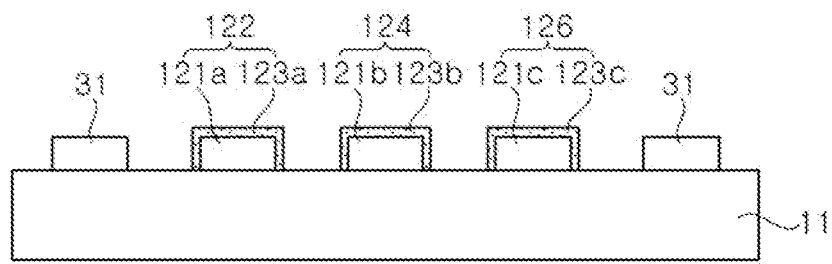
FIG. 10 is a schematic cross-sectional view taken along the line B-B of FIG. 9.

FIG. 9 is a schematic cross-sectional view illustrating a lighting apparatus according to another embodiment of the present disclosure, and FIG. 10 is a schematic cross-sectional view taken along the line B-B of FIG. 9.

Referring to FIG. 9 and FIG. 10, the lighting apparatus according to the present embodiment includes a substrate 11, a first light emitting unit 122, a second light emitting unit 124, a third light emitting unit 126 and a second light emitting diode 31. Since the substrate 11 and the second light emitting diode 31 are similar to those described with reference to FIG. 3 and FIG. 4, detailed descriptions thereof will be omitted to avoid redundancy.

Meanwhile, the first light emitting unit 122 includes a first first-light emitting diode 121*a* and a first wavelength converter 123*a*, the second light emitting unit 124 includes a first second-light emitting diode 121*b* and a second wavelength converter 123*b*, and the third light emitting unit 126 includes a first third-light emitting diode 121*c* and a third wavelength converter 123*c*.

In one embodiment, the first first- to first third-light emitting diodes 121*a*, 121*b*, and 121*c* may emit light having a central wavelength in a range of about 300 nm to about 420 nm, respectively. In particular, the first first- to first third-light emitting diodes 121*a*, 121*b*, and 121*c* may have a central wavelength in a range of about 400 nm to about 420 nm. These may be the same light emitting diodes within these ranges, or may be light emitting diodes having different central wavelengths.

Meanwhile, the first to third wavelength converters 123*a*, 123*b*, and 123*c* include a blue wavelength conversion substance for converting light emitted from the light emitting diode into blue light, respectively. The first to third wavelength converters 123*a*, 123*b*, and 123*c* may also include a green wavelength conversion substance for converting light emitted from the light emitting diode into green light and a red wavelength conversion substance for converting light emitted from the light emitting diode into red light, respectively. The blue conversion substance, the green wavelength conversion substance and the red wavelength conversion substance may be selected from the blue phosphor, the green phosphor and the red phosphor described with reference to FIG. 3 and FIG. 4. These phosphors may also be replaced with quantum dots.

Meanwhile, the first to third light emitting units 122, 124, and 126 may emit white light having different color temperatures. For this purpose, the first to third wavelength converters may include different wavelength conversion substances or different amounts of wavelength conversion substances.

In addition, the first to third light emitting units 122, 124, and 126 may be independently driven. For example, the first light emitting unit 122 may implement white light having a color temperature of 6000K or 6500K, the second light emitting unit 124 may implement white light having a color temperature of 2700K, and the third light emitting unit 126 may implement white light having a color temperature of 4000K. As a result, the first to third light emitting units are selectively driven for a day, and thus the color temperature of the lighting apparatus may be changed in accordance with the change of sunlight. In some embodiments, the first to third light emitting units 122, 124, and 126 may be driven together, and may implement white light having a desired color temperature together.

Meanwhile, in irradiance spectrum of light emitted to the outside, irradiance of the central wavelength of light generated by each of the light emitting diodes 121*a*, 121*b*, and 121*c* in the first to third light emitting units 122, 124, and 126 and emitted to the outside without wavelength conversion is smaller than that of a peak wavelength of blue light emitted from the corresponding respective wavelength converters 123*a*, 123*b*, and 123*c*. Accordingly, eye diseases or skin diseases may be prevented by the lighting apparatus.

The second light emitting diode 31 may be driven together when at least one of the first to third light emitting units 122, 124, and 126 is driven. In addition, the second light emitting diode 31 may be driven independently of the first to third light emitting units 122, 124, and 126, and thus the second light emitting diode 31 may be driven even when the first to third light emitting units 122, 124, and 126 are not driven. Therefore, the second light emitting diode 31 may operate to perform the cell activating function even at night when the lighting apparatus is not used.

Meanwhile, the first to third light emitting units 122, 124, and 126 may be disposed so that each of the light emitting units is evenly distributed. In the present embodiment, although the second light emitting diodes 31 are shown to be disposed outside of locations where the first to third light emitting units 122, 124, and 126 are disposed, the present disclosure is not necessarily limited thereto, and may be disposed together with the first to third light emitting units.

Moreover, in this embodiment, the first first- to first third-light emitting diodes may be disposed more than the second light emitting diodes in the lighting apparatus, respectively. However, the present disclosure is not necessarily limited thereto.

In the present embodiment, the first to third light emitting units 122, 124, and 126 have structures where the wavelength converters 123*a*, 123*b*, and 123*c* surround the light emitting diodes 121*a*, 121*b*, and 121*c*. For example, these light emitting units may be chip scale packages. However, the present disclosure is not limited thereto, but the light emitting units 122, 124, and 126 may be light emitting devices in the form of a conventional package.

In addition, in the present embodiment, it is described that the color temperature is changed by using three kinds of light emitting units 122, 124, and 126, but four or more kinds of light emitting units or two kinds of light emitting units may be used to implement various color temperatures. For example, by adjusting intensities of the first light emitting unit 122 and the second light emitting unit 124, light of an intermediate color temperature between the color temperatures of the first light emitting unit and the second light emitting unit may be variously implemented, and, accordingly, the third light emitting unit 126 may be omitted. Alternatively, it is possible to implement light of various color temperatures by including more light emitting units and driving them in turn.

Moreover, in the present embodiment, the first first- to first third-light emitting diodes 121a, 121b, and 121c are all described as having the central wavelength in the range of 300 nm to 420 nm, but the present disclosure is not necessarily limited thereto. A light emitting unit having a low color temperature, for example, the second light emitting unit 124 may include a blue light emitting diode and a wavelength converter. Therefore, the first second-light emitting diode 121b may have a central wavelength in a range of 300 nm to 470 nm. The light emitting unit having the low color temperature may be used without causing eye diseases or skin diseases because the intensity of blue light emitted to the outside is weak even when the blue light emitting diode is used as in the related art. The third light emitting unit 126 representing the intermediate color temperature may also employ the blue light emitting diode if the intensity of blue light emitted to the outside is weak. However, since the first light emitting unit 122 has a high color temperature, it is necessary to employ a light emitting diode having a central wavelength of about 420 nm or less.

Meanwhile, when the second light emitting unit 124 or the third light emitting unit 126 employs the blue light emitting diode, they may use a green phosphor and a red phosphor, or may use an orange phosphor, instead of using the blue phosphor.

Figure 11:
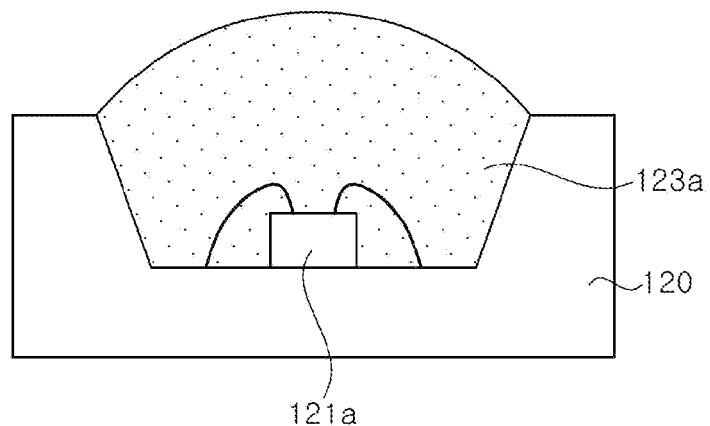
FIG. 11 is a schematic cross-sectional view illustrating a light emitting unit according to another embodiment of the present disclosure.

FIG. 11 is a schematic cross-sectional view illustrating a light emitting unit according to another embodiment of the present disclosure. Herein, FIG. 11 schematically shows a light emitting device in the form of a conventional package.

Referring to FIG. 11, the first light emitting unit 122 includes a first first-light emitting diode 121a and a first wavelength converter 123a. The first first-light emitting diode 121a may be mounted in a cavity of a housing 120, and the first wavelength converter 123a covers the light emitting diode 121a in the cavity. Meanwhile, the first first-light emitting diode 121a may be electrically connected to lead electrodes through bonding wires.

The package of FIG. 11 is an example, and various kinds of packages may be used. In addition, the first wavelength converter 123a may cover the light emitting diode 121a in various shapes.

Meanwhile, although the first light emitting unit 122 is representatively described here, the second light emitting unit 124 and the third light emitting unit 126 may also be light emitting devices having the same package form.

In addition, the second light emitting diode 31 may also be provided as a light emitting device in a package form and mounted on the substrate 11. However, the second light emitting diode 31 may be covered with a transparent molding member instead of being covered with the wavelength converter.

Lighting apparatuses of the present disclosure may change the color temperature of white light in response to the change in the color temperature of sunlight over time. Furthermore, the lighting apparatuses of the present disclosure may change the color temperature of white light in consideration of the change in the color temperature of sunlight according to a region.

Figure 12:
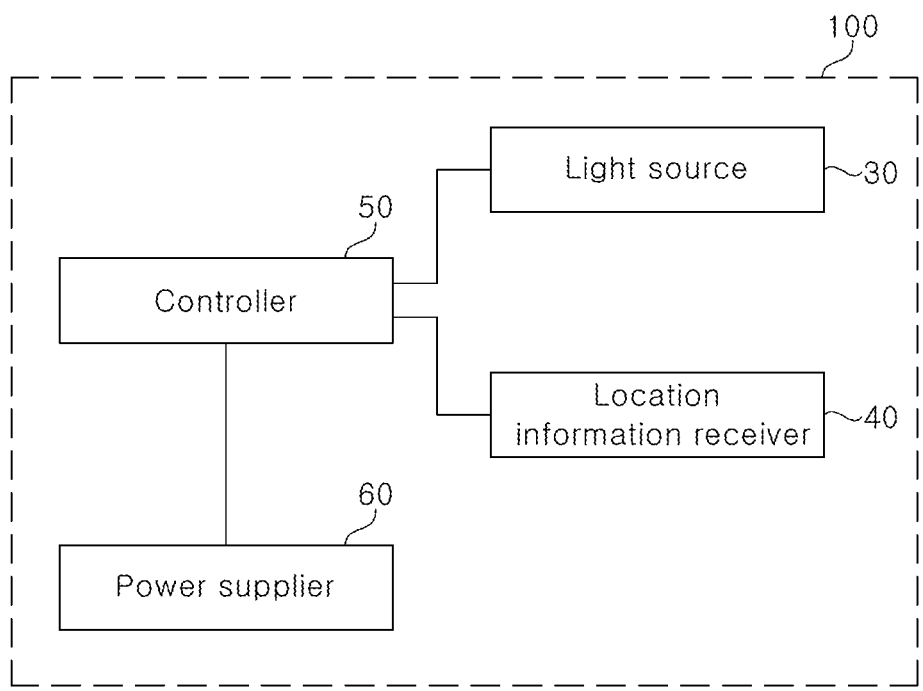
FIG. 12 is a block diagram illustrating a lighting apparatus according to an embodiment of the present disclosure.

FIG. 12 is a block diagram illustrating a lighting apparatus 100 according to an embodiment of the present disclosure.

Referring to FIG. 12, the lighting apparatus 100 according to an embodiment of the present disclosure includes a light source 30 emitting light, a location information receiver for receiving location information, and a controller 50 receiving the location information from the location information receiver and controlling a dose of light emitted from the light source 30. Herein, the location information refers to information that can be obtained by using a global positioning system (GPS). Meanwhile, the light source 30 refers to a white light source that implements white light, and is an arbitrary light source capable of changing the color temperature. For example, the light source 30 may be the white light emitting device including the first light emitting diode 21 and the wavelength converter 23 or the first to third light emitting units 122, 124, and 126, but the light source 30 is not limited thereto.

The location information receiver 40 receives the location information from a satellite using GPS to calculate current location information of the lighting apparatus 100. That is, the location information may include latitude and longitude, and the location information such as current latitude and longitude of the lighting apparatus 100 may be obtained by location information received by the location information receiver 40. The location information obtained by using the location information signal is provided to the controller 50.

The controller 50 calculates a dose of light to be emitted by the light source 30 based on the location information provided by the location information receiver 40, and controls the light source 30 to emit light as much as the dose of light. In other words, the controller 50 may control whether the light is emitted or not, an amount of light, an intensity of light, an emission time, and the like. The controller 50 may also control a dose of light to be emitted from the second light emitting diode 31 to sterilize pathogenic microorganisms together with the dose of the light source 30. In particular, the controller 50 may control the dose of the light emitted from the second light emitting diode 31 according to the dose of the white light source 30.

The power supplier 60 is electrically connected to the controller 50 to supply power to the light source 30 and the location information receiver 40. In the drawing, the power supplier 60 is illustrated as suppling power to the light source 30 and the location information receiver 40 through the controller 50, but the present disclosure is not limited thereto. The light source 30 and the location information receiver 40 may be directly connected to the power supplier 60, respectively.

The light source 30 and the location information receiver 40 may be disposed on the substrate 11. However, the present disclosure is not limited thereto, and the location information receiver 40 may be disposed on a substrate different from the substrate 11 on which the light source 30 is disposed.

Sunlight is not irradiated at the same intensity to all places on the earth. As the latitude becomes lower, the dose of sunlight becomes larger, and, as the latitude becomes higher, the dose of sunlight becomes smaller. In addition, the altitude becomes higher, the dose of sunlight becomes larger, and, as the altitude becomes lower, the dose of sunlight becomes smaller. Accordingly, depending on which country and in which place a user of the lighting apparatus 100 is present, the time or degree of exposure to sunlight may vary.

In an embodiment of the present disclosure, a location of the lighting apparatus 100 is determined by using location information, a dose of sunlight is calculated at the location, and then the visible light corresponding to the dose of sunlight is irradiated to a user, and thus the user may obtain the effect of exposure to sunlight within a harmless limit to the human body.

This will be described with reference to the drawings.

Figure 13:
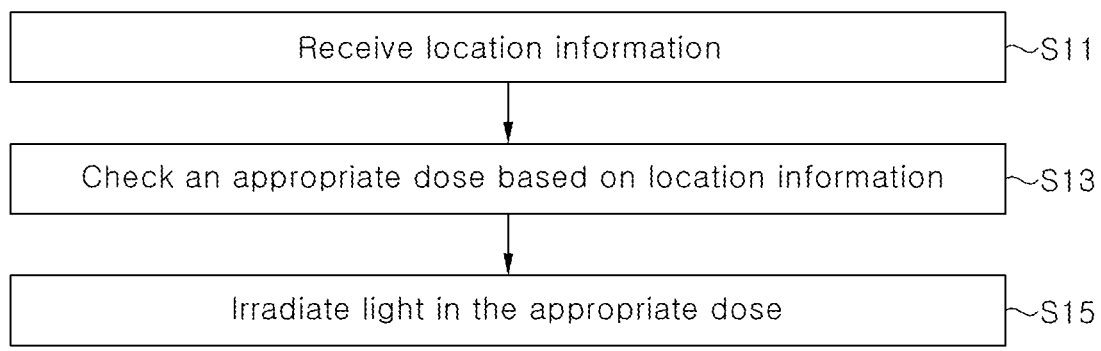
FIG. 13 is a flowchart illustrating a method of driving a light irradiation apparatus according to an embodiment of the present disclosure.

FIG. 13 is a flowchart illustrating a method of driving a light irradiation apparatus according to an embodiment of the present disclosure.

Referring to FIG. 13, a location information receiver receives location information: S11. For example, it may be determined that the light irradiation apparatus is located in city B of country A according to the location information obtained from the location information receiver.

The received location information is provided to a controller, and the controller checks or calculates an appropriate dose of light to be emitted by the light irradiation apparatus based on the location information: S13. For example, when city B of country A is determined, in addition to the latitude and longitude information of city B of country A, information such as sunrise time, sunset time, and average amount of sunshine may be calculated. When using the latitude and longitude information, the sunrise and sunset time on the latitude and longitude may be easily confirmed, and thus the controller may be configured to determine whether it is a day or night using an algorithm that calculates the sunrise and sunset time on the current latitude and longitude.

Using the information such as sunrise time, sunset time, and average amount of sunshine, the controller may calculate the turn-on time, turn-off time, light intensity, etc. of the light source, so as to have a similar dose to that of the actual sunlight, that is, to have an appropriate dose. In particular, the controller may properly adjust whether the light source is irradiated or not by accurately determining the day or night light without adding an illumination sensor.

The information such as sunrise time, sunset time, and average amount of sunshine at each location may be stored in a separate memory in the controller, or may be easily obtained by accessing a separate internet network or the like.

The controller is configured to irradiate light in a dose corresponding to the appropriate dose calculated by turning on or off the light source, to the user from the light source: S15. The user may be irradiated with the dose substantially the same as that of sunlight at the place where he or she is, even if he or she does not go outdoors.

According to an embodiment of the present disclosure, even if the user is in an environment where he or she is hardly exposed to sunlight, for example, living indoors for a long time, being in a hospital room or a limited space, or mainly being active at night, light similar to sunlight at the present location may be provided in an appropriate dose for a suitable time. Accordingly, the user may be in a familiar environment, psychological stability of the user may be possible, and the irradiation time may also be controlled by setting the sunrise or sunset time, thereby easily recovering the daily biorhythm.

In the embodiment described above, although it has been described that a single light is used instead of sunlight based on the location information, an embodiment of the present disclosure is not limited thereto. The light irradiation apparatus may be used as a correction light source that compensates for a lack of external light in the presence of natural light, ie, external light emitted from sunlight or lighting apparatuses. For example, in a place with high latitude, a amount of sunshine may be significantly lower than in a region with low latitude, in which case it is necessary to compensate for the lack of sunshine. When the amount of sunshine is low, not only light in the visible light wavelength band irradiated to the user may be insufficient, but also light in the ultraviolet light wavelength band may be insufficient. In this case, the light irradiation apparatus according to the embodiment of the present disclosure may serve to compensate for the insufficient light by additionally irradiating light of the visible light wavelength band and light of the ultraviolet wavelength band.

Figure 14:
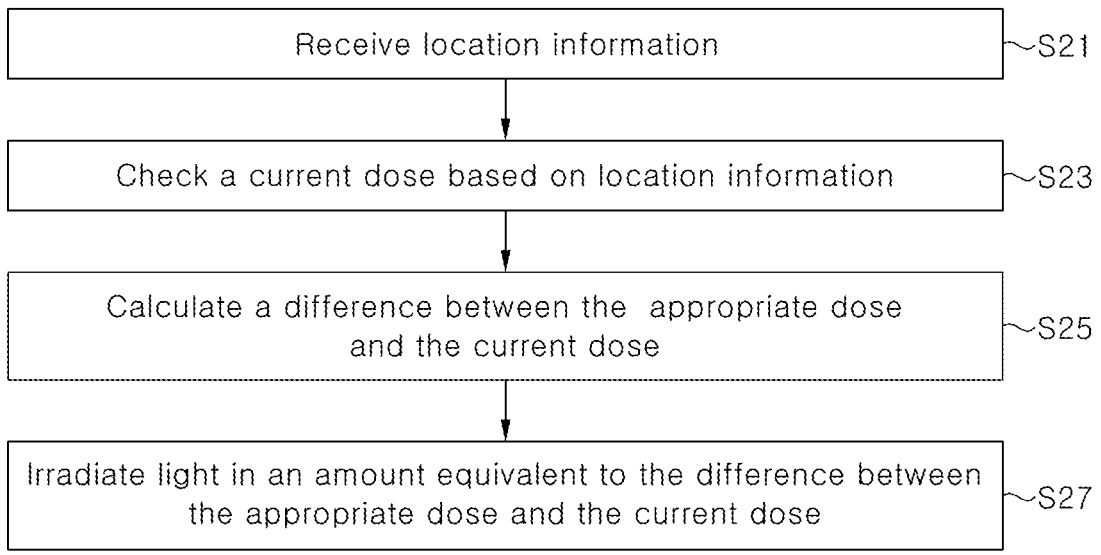
FIG. 14 is a flowchart illustrating a method of driving the light irradiation apparatus according to an embodiment of the present disclosure.

FIG. 14 is a flowchart illustrating a method of driving the light irradiation apparatus according to an embodiment of the present disclosure.

Referring to FIG. 14, a location information receiver receives location information: S21. For example, it may be determined that the light irradiation apparatus is located in city D of country C according to the location information obtained from the location information receiver.

The received location information is provided to a controller, and the controller calculates information such as sunrise time, sunset time, and average amount of sunshine at a current location based on the location information, and, using the information such as sunrise time, sunset time, and average amount of sunshine, calculates a current dose of actual sunlight: S23.

Next, a difference between an appropriate dose required for the user and the current dose is calculated: S25. For example, in the case of city D of country C which is located in a region with high latitude and an amount of sunshine is insufficient, an amount of sunshine actually required is the appropriate dose, and a value obtained by subtracting the current dose from the appropriate dose is an insufficient dose. The appropriate dose required for the user may be stored in a separate memory or the like in the controller, or may be easily obtained by connecting to a separate internet network or the like.

The controller is configured to irradiate light in a dose corresponding to the difference between the appropriate dose calculated by turning on or off the light source and the external light dose, that is, light with the insufficient dose, to a target object from the light source: S27.

The user may be irradiated with the predetermined light in the dose most appropriate to the user regardless of the place where he or she is. that is most suitable for the user regardless of where he or she is.

Although various lighting apparatuses have been described above, the present disclosure is not limited to these specific embodiments. In addition, the lighting apparatus may be installed in not only an indoor living space but also an indoor space used by a plurality of people, such as a hospital or an airport. Thus, a lighting system in which the lighting apparatus is installed may also be provided. This lighting system may be suitable for producing the cell activating substance, and may operate the lighting apparatus to effectively produce the cell activating substance even when people are inactive.

Although some exemplary embodiments have been described herein, it should be understood that these embodiments are provided for illustration only and are not to be construed in any way as limiting the present disclosure. It should be understood that features or components of one exemplary embodiment may also be applied to other exemplary embodiments without departing from the spirit and scope of the present disclosure.

The invention claimed is:

1. A lighting apparatus, comprising:
a white light emitting device including at least one first light emitter and a wavelength converter to implement white light;
at least one second light emitter configured to emit light having a peak wavelength different from a peak wavelength of light emitted by the at least one first light emitter; and
a controller configured to control the white light emitting device and the at least one second light emitter,
wherein:
the at least one first light emitter is configured to emit the light having the peak wavelength in a range of blue light;
the white light emitting device is configured to emit light having a peak wavelength in a range of about 430 nm to about 470 nm;
the at least one second light emitter is configured to emit the light having the peak wavelength in a range of about 605 nm to about 935 nm;
the wavelength converter includes a plurality of wavelength conversion substances to convert the light of the at least one first light emitter into white light; and
the light emitted by the at least one second light emitter includes a region in an irradiance spectrum having an irradiance that is greater than an irradiance of light emitted from the white light emitting device at a same wavelength.

2. The lighting apparatus of claim 1, wherein the at least one second light emitter is spaced apart from the wavelength converter.

3. The lighting apparatus of claim 2, wherein the at least one second light emitter is spaced apart from the white light emitting device.

4. The lighting apparatus of claim 2, wherein the light emitted from the at least one second light emitter is emitted to an outside of the lighting apparatus without passing through the wavelength converter.

5. The lighting apparatus of claim 1, wherein an irradiance of the light generated by the at least one second light emitter and emitted to an outside of the lighting apparatus is greater than an irradiance of a red light wavelength-converted by the wavelength converter on the at least one first light emitter and emitted to the outside of the lighting apparatus.

6. The lighting apparatus of claim 5, wherein a number of first light emitters of the at least one first light emitter is greater than a number of second light emitters of the at least one second light emitter.

7. The lighting apparatus of claim 1, wherein an irradiance of light generated by the at least one second light emitter and emitted to an outside of the lighting apparatus is less than or equal to 570 W/m$^2$.

8. The lighting apparatus of claim 1, further comprising a circuit board on which the at least one first light emitter and the at least one second light emitter are mounted.

9. A lighting apparatus, comprising:
a white light emitting device including at least one first light emitter and a wavelength converter to implement white light; and
at least one second light emitter configured to emit light having a peak wavelength different from a peak wavelength of light emitted by the at least one first light emitter; and
a controller configured to control the white light emitting device and the at least one second light emitter,
wherein:
the at least one first light emitter is configured to emit the light having the peak wavelength in a range of blue light;
the white light emitting device is configured to emit light having a peak wavelength in a range of about 430 nm to about 470 nm;
the at least one second light emitter is configured to emit the light having the peak wavelength in a range of about 605 nm to about 935 nm;
the wavelength converter includes a plurality of wavelength conversion substances to convert the light of the at least one first light emitter into white light; and
the light emitted by the at least one second light emitter includes a region in an irradiance spectrum having an irradiance of the light generated by the at least one second light emitter and emitted to an outside of the lighting apparatus without wavelength conversion that is greater than an irradiance of the light generated by the at least one first light emitter and emitted to the outside of the lighting apparatus without wavelength conversion.

10. The lighting apparatus of claim 9, wherein the at least one second light emitter is spaced apart from the wavelength converter.

11. The lighting apparatus of claim 10, wherein the light emitted from the at least one second light emitter is emitted to the outside of the lighting apparatus without passing through the wavelength converter.

12. The lighting apparatus of claim 9, wherein an irradiance of light generated by the at least one second light emitter and emitted to the outside of the lighting apparatus is greater than an irradiance of red light wavelength-converted by the wavelength converter on the at least one first light emitter and emitted to the outside of the lighting apparatus.

13. The lighting apparatus of claim 12, wherein a number of first light emitters of the at least one first light emitter is greater than a number of second light emitters of the at least one second light emitter.

14. The lighting apparatus of claim 9, wherein an irradiance of light generated by the at least one second light emitter and emitted to the outside of the lighting apparatus is less than or equal to 570 W/m$^2$.

15. A lighting apparatus, comprising:
a white light emitting device including at least one first light emitter and a wavelength converter to implement white light;
at least one second light emitter configured to emit light having a peak wavelength different from a peak wavelength of light emitted by the at least one first light emitter; and
a controller configured to control the white light emitting device and the at least one second light emitter,
wherein:
the at least one first light emitter is configured to emit the light having the peak wavelength in a range of blue light;
the white light emitting device is configured to emit light having a peak wavelength in a range of about 430 nm to about 470 nm:
the at least one second light emitter is configured to emit the light having the peak wavelength that is longer than the peak wavelength of the light emitted by the at least one first light emitter;
the wavelength converter includes a plurality of wavelength conversion substances to convert the light of the at least one first light emitter into white light; and the light emitted by the at least one second light emitter includes a region in an irradiance spectrum having an irradiance of the light generated by the at least one second light emitter and emitted to an outside of the lighting apparatus that is greater than an irradiance of light wavelength-converted by the wavelength converter on the at least one first light emitter and emitted to the outside of the lighting apparatus at a same wavelength.

16. The lighting apparatus of claim 15, wherein the at least one second light emitter is spaced apart from the wavelength converter.

17. The lighting apparatus of claim 16, wherein the light emitted from the at least one second light emitter is emitted to the outside of the lighting apparatus without passing through the wavelength converter.

18. The lighting apparatus of claim 15, wherein an irradiance of light generated by the at least one second light emitter and emitted to the outside of the lighting apparatus is greater than an irradiance of red light wavelength-converted by the wavelength converter on the at least one first light emitter and emitted to the outside of the lighting apparatus.

19. The lighting apparatus of claim 18, wherein a number of first light emitters of the at least one first light emitter is greater than a number of second light emitters of the at least one second light emitter.

20. The lighting apparatus of claim 15, wherein an irradiance of light generated by the at least one second light emitter and emitted to the outside of the lighting apparatus is less than or equal to 570 W/m$^2$.

\* \* \* \* \*